United States Patent [19]
Niemiec et al.

[11] Patent Number: 5,593,836
[45] Date of Patent: Jan. 14, 1997

[54] **PRIMERS AND PROBES FOR DETECTING *PNEUMOCYSTIS CARINII***

[76] Inventors: John T. Niemiec, 2071 San Jose Ave., Alameda, Calif. 94501; Karen K. Y. Young, 9943 Brunswick Ct., San Ramon, Calif. 94583

[21] Appl. No.: 448,204

[22] Filed: May 23, 1995

Related U.S. Application Data

[63] Continuation of Ser. No. 62,089, May 14, 1993, abandoned.
[51] Int. Cl.$^6$ .............................. C12Q 1/68; C07H 21/04
[52] U.S. Cl. .............................. 435/6; 536/23.1; 536/24.3
[58] Field of Search .............................. 435/6; 536/22.1, 536/24.3, 24.31

[56] References Cited

FOREIGN PATENT DOCUMENTS

| | | |
|---|---|---|
| 0327390 | 8/1989 | European Pat. Off. . |
| 9013669 | 11/1990 | WIPO . |
| 9102092 | 2/1991 | WIPO . |
| WO9102092A | 2/1991 | WIPO . |
| 9119005 | 12/1991 | WIPO . |
| 9402636 | 2/1994 | WIPO . |

OTHER PUBLICATIONS

Borensztein et al., Molecular and Cellular Probes 6:361–365 (1992).
Edman et al., 1988, "Ribosomal RNA Sequence Shows Pneumocystis carinii to be a Member of the Fungi" Nature 334: 519–522.
Lipschik et al., 1992, "Improved Diagnosis of Pneumocystis carinii Infection by Polymerase Chain Reaction on Induced Sputum and Blood" Lancet 340:203–206.
Medlin et al., 1988, "The Characterization of Enzymatically Amplified Eukaryotic 16S–like rRNA–Coding Regions" Gene 71:491–499.
Sogin and Edman, 1989, "A Self–Splicing Intron in the Small Subunit rRNA Gene of Pneumocystis carinii" Nucleic Acids Research 17(13): 5349–5359.
Wakefield et al., 1990, "Detection of Pneumocystis carinii With DNA Amplification" Lancet 336:451–453.
Wakefield et al., 1990, "Amplification of Mitochondrial Ribosomal RNA Sequences From Pneumocystis carinii DNA of Rat and Human Origin" Molecular and Biochemical Parasitology 43:69–76.
Kitada et al., 1991, "Diagnosis of Pneumocystis carinii Pneumonia by 5S Ribosomal DNA Amplification" J. Protozool. 38(6): 90S–91S.
Kitada et al., 1991, "Detection of Pneumocystis carinii Sequences by Polymerase Chain Reaction: Animal Models and Clinical Application to Noninvasive Specimens" J. Clinical Microbiology 29(9):1985–1990.
Sinclair et al., 1991, "Pneumocystis carinii Organisms Derived From Rat and Human Hosts are Genetically Distinct" Molecular and Biochemical Parasitology 45:183–184.
Cushion et al., 1993, "Evidence for Two Genetic Variants of Pneumocystis carinii Coinfecting Laboratory Rats" J. Clinical Microbiology 31(5):1217–1223.
Lee et al., 1993, "Nucleotide Sequence Variation in Pneumocystis carinii Strains That Infect Humans" J. Clinical Microbiology 31(3):754–757.
Stratagene Catalog (1988) p. 39.
GenBank Accession Nos. Q10826, Q10825, V10397, L19742 and L22158.

*Primary Examiner*—W. Gary Jones
*Assistant Examiner*—Ethan Whisenant

[57] ABSTRACT

Primers and probes can be used to detect nucleic acid from human strains of *Pneumocystis carinii* in a sample. The nucleotide sequence of a region of the 18S ribosomal RNA gene of a strain of *P. carinii* derived from humans is provided. The primers amplify regions of the 18S ribosomal RNA gene and hybridize to regions containing variability among strains. Probes hybridize to a regions within the amplified region that contain variability among strains.

11 Claims, 4 Drawing Sheets

\* AVERAGE OF TWO VALUES
\*\* AVERAGE OF FOUR VALUES

PRIMERS AND PROBES FOR DETECTING *PNEUMOCYSTIS CARINII*

This is a continuation of application Ser. No. 08/062,089, filed May 14, 1993, now abandoned.

BACKGROUND OF THE INVENTION

1. Field of the Invention

The present invention relates to methods and reagents for detecting the presence of nucleic acid from human strains of *Pneumocystis carinii* (*P. carinii*).

2. Description of Related Art

*P. carinii* is an opportunistic fungal pathogen that infects the lower respiratory tract. The fungal cysts and trophozoites cause severe pneumonia in humans immunocompromised as a result of AIDS, organ transplantation, bone marrow transplantation; or chemotherapy. *P. carinii* is the leading cause of morbidity and mortality in AIDS patients in the United States. Early diagnosis and treatment is essential to prevent mortality. Information relating to its taxonomic classification and characteristics can be found in Edman et al., 1988, *Nature* 334:519–522, incorporated herein by reference.

Initial methods for the diagnosis of *P. carinii* pneumonia (PCP) depended on the staining and microscopic examination of induced sputum, bronchial alveolar lavage (BAL) and transbronchial biopsy (TBB) specimens for evidence of the parasite. If PCP is suspected but an initial examination of an induced sputum sample is negative, the more invasive procedures of examining BAL or TBB specimens are required for diagnosis.

The invention of the polymerase chain reaction (PCR), a method for amplifying specific sequences of nucleic acids, makes possible the rapid detection of nucleic acids present in a cell in what was previously an undetectably low quantity (see U.S. Pat. Nos. 4,683,195; 4,683,202; and 4,965,188, each of which is incorporated herein by reference). Using PCR amplification, one can detect even a single copy of the target nucleic acid. Direct detection of an amplified nucleic acid sequence by hybridization with a sequence-specific oligonucleotide probe makes possible diagnostic tests that are specific enough to detect single nucleotide changes in sequence.

Recent attempts have been made to develop a diagnostic test for *P. carinii* using nucleic acid amplification techniques. Edman et al., 1988, supra disclose a sequence of a region of the 16S-like (18S) ribosomal RNA (rRNA) gene of a *P. carinii* strain derived from rats. PCT publication WO 90/13669, incorporated herein by reference, discloses detection probes based on the rat-derived sequence published in Edman et al., 1988, supra. Lipschik, 1992, *Lancet* 340:203–206, incorporated herein by reference, also discloses primers and probes based on the sequence disclosed in Edman et al., 1988, supra, and describes their use in a nested PCR.

PCR publication WO 91/02092 describes the use of nonspecific amplification primers from Merlin et at., 1988, *Gene* 71:491–499, both of which are incorporated herein by reference, and probes based on the sequence of the 18S rRNA gene from a human strain of *P. carinii*. The amplification primers used to amplify a region of the 18S rRNA gene were not specific to *P. carinii*. The detection probes described typically hybridized to several of the human, rat, and ferret strains of *P. carinii* tested.

Detection assays based on gene sequences obtained from rat strains of *P. carinii* may be less sensitive and less specific than one which could be designed based on gene sequences obtained from a human strain of *P. carinii* because of genotypic variation between rat and human isolates of *P. carinii*. Thus, it would be advantageous to provide assays comprising primers and probes based on gene sequences obtained from a human strain of *P. carinii*. Furthermore, because it is unknown if rat strains of *P. carinii* can infect humans, it is desirable that an assay be able to distinguish between rat and human strains of *P. carinii*. There is still a need for a rapid, efficient, and sensitive assay to identify the presence of *P. carinii* DNA which is specific for human strains of *P. carinii*.

SUMMARY OF INVENTION

The present invention provides a rapid and sensitive assay for the detection of *P. carinii* DNA. Further, the invention provides the nucleotide sequence of a region of the 18S ribosomal RNA (rRNA) gene of *P. carinii* isolated from human specimens. Primers and probes specific for human *P. carinii* 18S ribosomal RNA gene sequences are provided. Detection is accomplished by amplification by a polymerase chain reaction (PCR) using sequence specific primers followed by hybridization with a sequence specific probe. In a preferred embodiment of the invention, a microwell plate assay format is utilized.

One aspect of the invention relates to the sequence of a region of the 18S ribosomal RNA gene of *P. carinii* isolated from human specimens.

Another aspect of the invention relates to probes capable of detecting the presence of *P. carinii* nucleic acid and distinguishing between strains of *P. carinii*. The sequence specific probes are complementary to a variable region of the 18S rRNA gene within which sufficient heterogeneity exists among strains (isolated from human and non-human specimen) to enable the .origin of the target nucleic acid to be determined.

Another aspect of the invention relates to primers for amplifying a specific region of *P. carinii* nucleic acid. The sequence specific primers amplify a variable region of the 18S rRNA gene within which sufficient heterogeneity exists among strains (isolated from human and non-human specimen) to enable human strains of *P. carinii* to be identified by hybridization with sequence specific probes.

Another aspect of the invention relates to detection methods. One method for the detection of nucleic acid from a human strain of *P. carinii* in a sample comprises:

(a) amplifying a subsequence of the nucleic acid using oligonucleotide primers specific for the 18S ribosomal RNA gene of a human strain of *P. carinii;* and (b) detecting amplified nucleic acid subsequences.

Another method for the detection of *P. carinii* nucleic acid in a sample comprises:

(a) mixing the sample with an oligonucleotide probe specific for a subsequence of the 18S ribosomal RNA gene of a human strain of *P. carinii* under conditions wherein the probe binds to the subsequence to form a stable hybrid duplex; and (b) detecting hybrid duplexes formed between the subsequence and the probe.

Another method the detecting of *P. carinii* nucleic acid contained in a sample comprises:

(a) amplifying a subsequence of the nucleic acid using oligonucleotide primers specific for the 18S ribosomal RNA gene of *P. carinii;*

(b) mixing the amplified subsequence with an oligonucleotide probe specific for the subsequence under conditions wherein the probe binds to the subsequence to form a stable hybrid duplex; and (c) detecting hybrid duplexes formed between the subsequence and the probe.

Another aspect of the present invention relates to compositions for use as positive controls for detecting human strains of *P. carinii*.

Another aspect of the invention relates to kits. These kits take a variety of forms and comprise a sequence specific probe and instructions for using the kit ingredients. The kits can also comprise one or more amplification reagents, e.g., sequence specific primers provided by the present invention, polymerase, buffers, and nucleoside triphosphates. In a further embodiment, the kit may also comprise positive and negative controls.

DETAILED DESCRIPTION OF THE INVENTION

Figure 1:
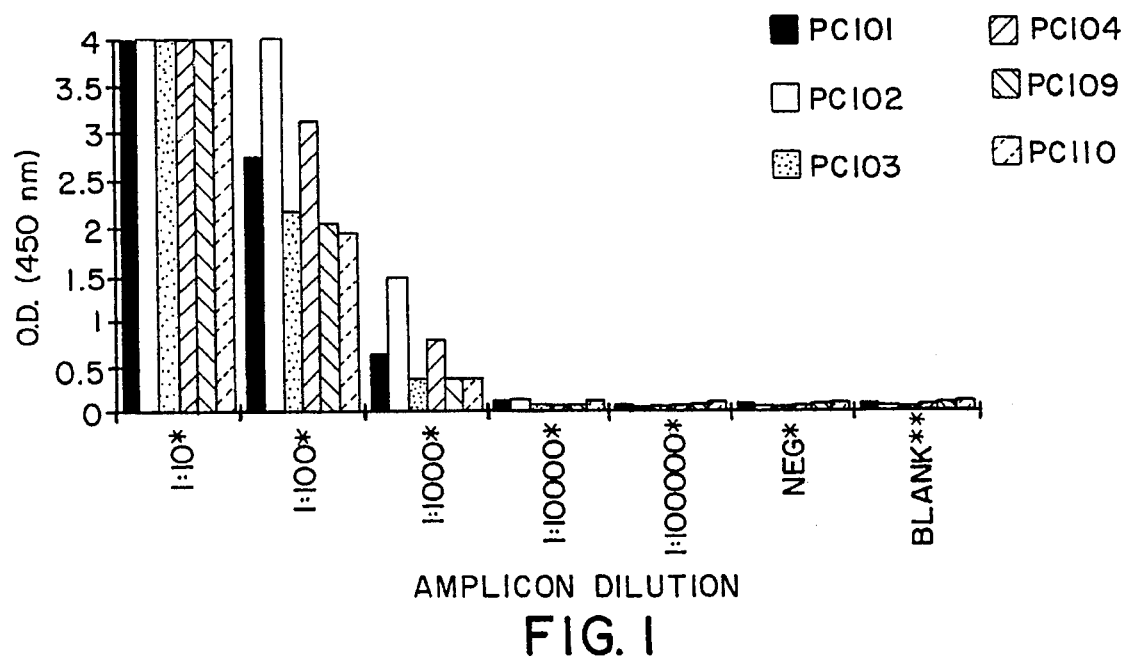
FIG. 1 shows the results of a comparison of probe sensitivities for 6 probes.

To aid in understanding the invention, several terms are defined below.

"Amplification reaction mixture" refers to an aqueous solution comprising the various reagents used to amplify a target nucleic acid. These include: enzymes, aqueous buffers, salts, target nucleic acid, and deoxynucleoside triphosphates. Depending upon the context, the mixture can be either a complete or incomplete amplification reaction mixture.

"Amplification reaction tube(s)" refers to a container suitable for holding the amplification reagents. Generally, the tube is constructed of inert components so as to not inhibit or interfere with the amplification system being used. Where the system requires thermal cycling of repeated heating and cooling, the tube must be able to withstand the cycling process and, typically, precisely fit the wells of the thermocycler.

"Amplification reagents" refer to the various buffers, enzymes, primers, deoxynucleoside triphosphates (both conventional and unconventional), and primers used to perform the selected amplification procedure.

"Amplicon" and "amplified product" refer to a nucleic acid formed as the product of an amplification reaction.

"Bind(s) substantially" refers to complementary hybridization between an oligonucleotide and a target sequence and embraces minor mismatches that can be accommodated by reducing the stringency of the hybridization media to achieve the desired priming for the PCR polymerases or detection of hybridization signal. An oligonucleotide which binds substantially is also referred to as "substantially complementary" to a target sequence.

"Hybridization" refers to the binding of two single stranded nucleic acids via complementary base pairing.

"Nucleic acid" refers to a deoxyribonucleotide or ribonucleotide polymer in either single-or double-stranded form, and unless otherwise limited, would encompass known analogs of natural nucleotides that can function in a similar manner as naturally occurring nucleotides.

"Nucleotide polymerases" refers to enzymes able to catalyze the synthesis of DNA or RNA from nucleoside triphosphate precursors. In the amplification reactions of this invention, the polymerases are template-dependent and typically add nucleotides to the 3'-end of the polymer being formed. The use of thermostable DNA polymerase in PCR is particularly described in U.S. Pat. Nos. 4,889,818 and 5,079,352, both of which are incorporated herein by reference.

The term "oligonucleotide" refers to a molecule comprised of two or more deoxyribonucleotides or ribonucleotides, such as primers, probes, nucleic acid fragments to be detected, and nucleic acid controls. The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al., 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, all of which are incorporated herein by reference.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The length of a primer depends on the intended use of the primer but typically ranges from 15 to 40 nucleotides; more typically from 20 to 35 nucleotides. Short primer molecules generally require cooler temperatures to form sufficiently stable hybrid complexes with the template. A primer need not reflect the exact sequence of the template but must be sufficiently complementary to hybridize with a template. The term "primer" may refer to more than one primer, particularly in the case where there is some ambiguity in the information regarding one or both ends of the target region to be amplified. For instance, if a region shows significant levels of polymorphism in a population, mixtures of primers can be prepared that will amplify alternate sequences.

The term "probe" refers to an oligonucleotide which binds through complementary base pairing to a subsequence of a target nucleic acid. Generally, the probes will have from 10 to 50 nucleotides, more preferably from 20 to 30 nucleotides of either of the complementary strands of the target nucleic acid. It will be understood by one of skill in the art that probes will typically substantially bind target sequences lacking complete complementarity with the probe sequence depending upon the stringency of the hybridization conditions.

A primer or probe can be labeled, if desired, by incorporating a label detectable by spectroscopic, photochemical, biochemical, immunochemical, or chemical means. For example, useful labels include $^{32}P$, fluorescent dyes, electron-dense reagents, enzymes (as commonly used in an ELISA), biotin, or haptens and proteins for which antisera or monoclonal antibodies are available. A label can also be used to "capture" the primer or probe, so as to facilitate the immobilization of either the primer, a primer extension product such as amplified DNA, or a probe on a solid support. For example, a preferred embodiment of the present invention provides that the probes are immobilized on a microwell plate.

In the disclosed embodiments of the invention, sequence specific primers and probes are provided. It will be apparent to those of skill in the art that, provided with those embodiments, additional sequence specific primers and probes can be prepared by, for example, the addition of nucleotides to either the 5' or 3' ends, which nucleotides are complementary to the target sequence or are not complementary to the target sequence. So long as primers comprise a sequence complementary to the target sequence of sufficient length to bind substantially during the amplification reaction and serve as a point of initiation for extension on the target sequences, such compositions are within the scope of the invention. So long as the probes comprise a sequence complementary to the target sequence of sufficient length to bind substantially in the hybridization assay and comprise at least one of the nucleotide sequence variants that are unique to human strains of *P. carinii* as disclosed in the sequence shown in Table 1, such compositions are within the scope of the invention.

The term "reverse transcriptase" refers to an enzyme that catalyzes the polymerization of deoxyribonucleoside triphosphates to form primer extension products that are complementary to a ribonucleic acid template. The enzyme initiates synthesis at the 3'-end of the primer and proceeds toward the 5'-end of the template until synthesis terminates. Examples of suitable polymerizing agents that convert the RNA target sequence into a complementary, copy-DNA (cDNA) sequence are murine leukemia virus reverse transcriptase (MuLV), arian myeloblastosis virus reverse transcriptase, and *Thermus thermophilus* DNA polymerase, a thermostable DNA polymerase with reverse transcriptase activity developed and manufactured by Hoffmann-La Roche Inc. and commercially available from Perkin Elmer (Norwalk, Conn.).

The terms "sequence-specific oligonucleotide" and "SSO" refer to oligonucleotides that have a sequence, called a hybridizing region, exactly complementary to the sequence to be detected which under sequence-specific, stringent hybridization conditions will hybridize only to that exact complementary target sequence. Stringent hybridization conditions are well known in the art (see, e.g., Sambrook et at., 1985, *Molecular Cloning—A Laboratory Manual,* Cold Spring Harbor Laboratory, Cold Spring Harbor, N.Y., incorporated herein by reference). Stringent conditions are sequence dependent and will be different in different circumstances. Generally, stringent conditions am selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.2 molar at pH 7 and the temperature is at least about 60° C., Relaxing the stringency of the hybridizing conditions will allow sequence mismatches to be tolerated; the degree of mismatch tolerated can be controlled by suitable adjustment of the hybridization conditions. Depending on the sequences being analyzed, one or more sequence-specific oligonucleotides may be employed. The term "SSO probe" is used interchangeably with SSO.

Wu et al., 1991, *DNA and Cell Biology* 10(3):233–238, which is incorporated herein by reference, provides a formula for estimating the optimum annealing temperature for PCR for any particular primer/template duplex. The nearest neighbor thermodynamic data of Breslauer et al., 1986, *Proc. Natl. Acad. Sci.* 83:3746–3750; as well as methods described in Wallace et al., 1979, *Nuc. Acids Res.* 6:3543–3557, which are incorporated herein by reference, exemplify empirical formulae for estimating Tm. Although Tm is generally slightly higher than the optimum annealing temperature for PCR, calculating Tm provides a guidance for one of ordinary skill in the art to empirically determine suitable temperatures for practicing the present invention.

The term "subsequence" refers herein to a nucleotide sequence contained within another sequence.

The term "target region" refers to a region of a nucleic acid to be analyzed.

The term "thermostable polymerase enzyme" refers to an enzyme that is relatively stable to heat and catalyzes the polymerization of nucleoside triphosphates to form primer extension products that are complementary to one of the nucleic acid strands of the target sequence. The enzyme initiates synthesis at the 3'-end of the primer and proceeds toward the 5'-end of the template until synthesis terminates. A purified thermostable polymerase enzyme is described more fully in U.S. Pat. No. 4,889,818, incorporated herein by reference, and is developed and manufactured by Hoffmann-La Roche Inc. and commercially available from Perkin Elmer (Norwalk, Conn.).

The terms "upstream" and "downstream" refer herein to relative positions along a nucleotide sequence. The upstream end of a sequence is the 5' end, the downstream end is the 3' end. A region is referred to as upstream relative to another region if it is more towards the 5' end of a sequence, and vice versa. Primers are designated as upstream or downstream primers based on the designation of their hybridization region along the target sequence oriented as in the Sequence Listing.

The present invention provides a rapid and sensitive PCR-based assay for the detection of *P. carinii*. Primers and probes specific for 18S rRNA gene sequences from human isolates of *P. carinii* are provided. Following PCR amplification of 18S rRNA gene sequences with sequence specific primers, detection of the amplified product is accomplished either by gel electrophoretic analysis or by hybridization of the amplified product with sequence specific probes. Applicable hybridization assay formats include both forward and reverse dot blot hybridization assays; both of which can be carried out conveniently in a microtiter plate; see U.S. Pat. No. 5,232,829, incorporated herein by reference.

The present invention provides the newly determined nucleotide sequence from a region of the 18S rRNA gene of *P. carinii* isolated from human specimens. Within this region are sequence variations which differentiate the human isolate sequence both from sequences obtained from non-human isolates and from sequences obtained from related fungi; the nucleotide sequence of this region was found to be conserved among human isolates of *P. carinii*. The sequence specific oligonucleotide probes of the present invention hybridize to variable regions of the 18S rRNA gene which contain the inter-strain sequence variability. Consequently, under stringent hybridization conditions as described in the Examples, below, probe hybridization occurs only with nucleotide sequence variants obtained from human isolates.

An assay based on primers and probes designed from the sequence of human *P. carinii* can be designed to achieve the maximum specificity possible (single base pair discrimination) while not sacrificing sensitivity. An assay based on primers and probes designed from a rat-strain sequence may not realize the same level of sensitivity or specificity due to sequence variation between rat and human strains of *P. carinii*. Relaxing the hybridization conditions to allow for base mismatches decreases the specificity, but may be necessary to avoid false negatives that can occur if the human-strain sequence differs from the rat-strain sequence in a probe hybridizing region. The present invention provides both primers and probes based on the human-strain sequence provided.

The nucleotide sequence of the region of the 18S rRNA gene obtained from a human isolate of *P. carinii* is provided below as SEQ ID No. 1. The letter "N" indicates that the base identity is unknown.

complementary to the human strain sequence and incorporate base changes relative to the rat strain sequence. Amplification with a primer pair selected from PC21 (SEQ ID No. 2), PC31 (SEQ ID No. 3), and PC41 (SEQ ID No. 4) for the upstream primer and PC22 (SEQ ID No. 5), PC32 (SEQ ID No. 6), and PC42 (SEQ ID No. 7) for the downstream primer produces a 418 base pair product corresponding to bases 494 to 911 in SEQ ID No. 1. In a preferred embodiment of the invention, amplification is carried out with the primer pair PC41 (SEQ ID No. 4) and PC22 (SEQ ID No. 5), which functions efficiently in the amplification of sequences from human isolates of *P. carinii* without simultaneously amplifying sequences from non *P. carinii* organisms. An assay of primer specificity is described in Example 12, below. Importantly, the primers do not amplify sequences from four fungi found in oral or pulmonary samples from immunocompromised individuals and, hence, which may coinfect a sample, *Blastomyces dermatitidis, Candida albicans, Coccidioides immitis, Histoplasma capsulatum;* and human genomic DNA, which is present in any clinical sample.

TABLE 1

18S rRNA Gene Sequence

SEQ ID No. 1–5'-

| | | | | | | |
|---|---|---|---|---|---|---|
| TGTTGGTTTC | TAGGACCCCT | GAATGATTAA | TAGGGACAGT | TGGGGGCATT | AGTATTCAAT | 60 |
| TGTCAGAGGT | GAAATTCTTA | GATTTATTGA | AGACTAACTA | CTGCGAAAGC | ATTTGCCAAG | 120 |
| GATGTTTTCA | TTAATCAAGA | ACGAAAGTTA | GGGGATCGAA | GACGATCAGA | TACCGTCGTA | 180 |
| GTCTTAACCA | TAAACTATGC | CGACTAGAGA | TCGGGCGATG | TTTTTTTCTT | GACTCGCTCG | 240 |
| GCATCTTATG | AGAAATCAAA | GTCTTCGGGT | TCCGGGGGGA | GTATGGTCGC | AAGGCTGAAA | 300 |
| CTTAAAGGAA | TTGACGGAAG | GGCACCACCA | GGAGTGGAGC | CTGCGGCTTA | ATTTGACTCA | 360 |
| ACACGGGGAA | ACTCACCAGG | TCCAGACATA | GTAAGGATTG | ACAGATTGAG | AGCTCTTTCT | 420 |
| TGATTCTATG | GGTGGTGGTG | CATGGCCGTT | CTTAGTTGGT | GAAGTGATTT | GTCTGCTTAA | 480 |
| TTGCGATAAC | GAACGAGACC | TTAACCTACT | AAATAGCCAG | ATTAGCTTTT | GCTGATCGCA | 540 |
| GGCTTCTTAG | AGGGACTGTT | GGCATGAAGC | CAATGGAAGT | TTGAGGCAAT | AACAGGTCTG | 600 |
| TGATGCCCTT | AGATGTTCTG | GGCCGCACGC | GCGCTACACT | GACAGAGCCA | GCAAGTTCAT | 660 |
| TTCCTTGACC | GAAAGGTTTG | GGTAATCTTG | TGAAACTCTG | TCGTGCTGGG | GATAGAGCAT | 720 |
| TGCAATTATT | GCTCTTCACC | GAGGAATTCC | TAGTAAGCGC | AAGTCATCAG | CTTGCGTTGA | 780 |
| TTATGTCCCT | GCCCTTTGTA | CACACCGCCC | GTCGCTACTA | CCGATTGAAT | GGCTTAGTGA | 840 |
| GGTCTTCGGA | CTGGCAGCGG | GCTGTTGCA | ACGATGACCC | ATTGCTGGAA | AGTTGATCAA | 900 |
| ATTTGGTCAT | TTAGAGGAAG | TAAAAGTCGC | NACAAGGTTT | CCGNAGGTGA | A | 951 |

The nucleotide substitutions which differentiate the human *P. carinii* and rat *P. carinii* sequences are shown in bold (base positions 18, 19, 508, 540, 632, 668, 778, 837, 855, 856, 857, 858, 862, 863, 876, 878, 884, and 930).

Oligonucleotide primers useful in the methods of the present invention catalyze the amplification of a subsequence of the 18S rRNA gene region shown in Table 1. Examples of useful primers are provided in Table 2, below. The hybridizing sequences of the primers are provided below.

In a preferred embodiment of the invention, detection of amplified nucleic acid sequences is accomplished by hybridizing the amplification product with an oligonucleotide probe and subsequently detecting the presence of hybridization duplexes. The hybridizing sequences of the probes of the present invention are provided below.

TABLE 2

| Primer | Sequence Listing | Hybridizing Sequence |
|---|---|---|
| PC21 | SEQ ID No. 2 | 5'-CGAGACCTTAACCTGCTAAATAGCCAGATTA |
| PC31 | SEQ ID No. 3 | 5'-CGAGACCTTAACCTGCTAAATAGCCAGATT |
| PC41 | SEQ ID No. 4 | 5'-CGAGACCTTAACCTACTAAATAGCCAGATTA |
| PC22 | SEQ ID No. 5 | 5'-AATGACCAAATTTGATCAACTTTCCAGCAA |
| PC32 | SEQ ID No. 6 | 5'-AATGACCAAATTTGAACAACTTTCCAGCAA |
| PC42 | SEQ ID No. 7 | 5'-AATGACCAAACTTGAACAACTTTCCAGCAA |

Odd number primers are upstream primers; even numbered primers are downstream primers. Primers PC22 (SEQ ID No. 5) and PC41 (SEQ ID No. 4) are specifically

TABLE 3

| Probe | Sequence Listing | Hybridizing Sequence |
| --- | --- | --- |
| PC102 | SEQ ID No. 8 | 5-TCATCGTTGCCAACAGCCCGCTGCCAGT |
| PC104 | SEQ ID No. 9 | 5-TTGCCAACAGCCCGCTGCCAGT |
| PC106 | SEQ ID No. 10 | 5-'GCTGCCAGTCCGAAGACCTCACTAA |
| PC108 | SEQ ID No. 11 | 5-'CGAAGACCTCACTAAGCCATTCAAT |
| PC110 | SEQ ID No. 12 | 5-TCAAGGAAATGAACTTGCTGGCTCT |
| PC112 | SEQ ID No. 13 | 5-TTCGGTCAAGGAAATGAACTTGCTGGCTCT |

The probes shown hybridize within the 418 base pair region (base 494 to base 911 of SEQ ID No. 1) amplified using a primer pair selected from PC21 (SEQ ID No. 2), PC31 (SEQ ID No. 3), and PC41 (SEQ ID No. 4) for the upstream primer and PC22 (SEQ ID No. 5), PC32 (SEQ ID No. 6), and PC42 (SEQ ID No. 7) for the downstream primer. Within this 418 base pair region, the probes hybridize in regions containing sequence variants that distinguish rat and human strains of P. carinii. A comparison of several probes is described in Example 10, below. An assay of probe specificity is described in Example 12, below.

DNA synthesis depends on the primer oligonucleotide hybridizing with the target sequence. Primer self-hybridization due to internal self-complementarity and hybridization between primer pairs can decrease the efficiency of amplification. Similarly, the detection assay depends on the probe hybridizing with its target sequence. The secondary structure arising from self-hybridization due to internal self-complementarity effects the binding efficiency and annealing temperature. The primers of the present invention were designed to avoid problems with self complementarity, pair complementarity and secondary structure. The probes of the present invention were designed to avoid problems with self complementarity, complementarity to primers PC41 (SEQ ID No. 4) and PC22 (SEQ ID No. 5), and secondary structure.

One skilled in the art will recognize that the human P. carinii sequence provided in Table 1, above, in conjunction with rat P. carinii sequence information available in GEN-BANK (accession no. X13687), enables the design of primers and probes which can differentiate between P. carinii strains. For example, a probe could be designed to hybridize to rat isolates of P. carinii without hybridizing to human isolates of P. carinii.

An important aspect of the present invention is the amplification of a region of the 18S rRNA gene. Although the polymerase chain reaction is the preferred amplification method, amplification of target sequences in a sample may be accomplished by any known method, such as ligase chain reaction (Wu and Wallace 1988, Genomics 4:560–569, incorporated herein by reference), the TAS amplification system (Kwoh et al., 1989, Proc. Natl. Acad. Sci. U.S.A. 86:1173–1177, incorporated herein by reference); and self-sustained sequence replication (Guatelli et al., 1990, Proc. Natl. Acad. Sci. U.S.A. 87:1874–1878, incorporated herein by reference), each of which provides sufficient amplification so that the target sequence can be detected by nucleic acid hybridization to an SSO probe. Alternatively, methods that amplify the probe to detectable levels can be used, such as Qβ-replicase amplification (Kramer and Lizardi, 1989, Nature 339:401–402, and Lomeli et al., 1989, Clin. Chem. 35:1826–1831, both of which are incorporated herein by reference).

The PCR process is well known in the art (see U.S. Pat. Nos. 4,683,195; 4,683,202; and 4,965,188, each of which is incorporated herein by reference). In general, to amplify a target nucleic acid sequence in a sample by PCR, the sequence must be accessible to the components of the amplification system. This accessibility is ensured by isolating the nucleic acids from the sample. A variety of techniques for extracting nucleic acids from biological samples are known in the art. For example, see those described in Higuchi et al., 1989, in PCR Technology (Erlich ed., Stockton Press, New York), incorporated herein by reference. Alteratively, if the sample is fairly readily disruptable, the nucleic acid need not be purified prior to amplification by the PCR technique, i.e., if the sample is comprised of cells, particularly peripheral blood lymphocytes or aminiocytes, lysis and dispersion of the intracellular components can be accomplished merely by suspending the cells in hypotonic buffer.

Each cycle of the PCR involves the separation of the nucleic acid duplex formed by primer extension. In a preferred embodiment of the PCR process, strand separation is achieved by heating the reaction to a sufficiently high temperature for an effective time to cause the denaturation of the duplex, but not to cause an irreversible denaturation of the polymerase (see U.S. Pat. No. 4,965,188). Typical heat denaturation involves temperatures ranging from about 80° C. to 105° C. for times ranging from seconds to minutes. Strand separation, however, can be accomplished by any suitable denaturing method including physical, chemical, or enzymatic means.

No matter how strand separation is achieved, however, once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

Template-dependent extension of primers in PCR is catalyzed by a polymerizing agent in the presence of adequate amounts of four deoxyribonucleoside triphosphates (dATP, dGTP, dCTP, and dTTP; dUTP is used in place of or in addition to dTTP if the UNG sterilization system described below is incorporated) in a reaction medium comprised of the appropriate salts, metal cations, and pH buffering system. Suitable polymerizing agents are enzymes known to catalyze template-dependent DNA synthesis. Examples of polymerases suitable for use with a DNA template include E. coli DNA polymerase I or the Klenow fragment of that enzyme, $T_4$ DNA polymerase, and Taq polymerase, a heat stable DNA polymerase isolated from Thermus aquaticus, developed and manufactured by Hoffmann-La Roche Inc. and commercially available from Perkin Elmer (Norwalk, Conn.). The latter enzyme is widely used in the amplification and sequencing of nucleic acids. The reaction conditions for using Taq polymerases are known in the art and are described in Gelfand, 1989, in *PCR Technology, supra.* Polymerizing agents suitable for synthesizing a complementary, copy DNA (cDNA) sequence from the RNA template are reverse transcriptase (RT), such as avian myeloblastosis virus RT, or *Thermus thermophilus* DNA polymerase, a thermostable DNA polymerase with reverse transcriptase activity developed and manufactured by Hoffmann-La Roche Inc. and commercially available from Perkin Elmer (Norwalk, Conn.). Typically, the RNA template is heat degraded during the first denaturation step after the initial reverse transcription step leaving only DNA template for subsequent amplification.

If 18S rRNA is to be amplified, an initial reverse transcription (RT) step is carried out to create a DNA copy (cDNA) of the RNA. PCT patent publication No. WO 91/09944, incorporated herein by reference, describes high temperature reverse transcription by a thermostable polymerase that also functions in PCR amplification. High temperature RT provides greater primer specificity and improved efficiency. U.S. Pat. No. 5,310,652 incorporated herein by reference, describes a "homogeneous RT-PCR" in which the same primers and polymerase suffice for both the reverse transcription and the PCR amplification steps, and the reaction conditions are optimized so that both reactions occur without a change of reagents. *Thermus thermophilus* DNA polymerase, a thermostable DNA polymerase that can function as a reverse transcriptase, is used for all primer extension steps, regardless of template. Both processes can be done without having to open the tube to change or add reagents; only the temperature profile is adjusted between the first cycle (RNA template) and the rest of the amplification cycles (DNA template).

Those skilled in the art will know that the PCR process is most usually carried out as an automated process with a thermostable enzyme. In this process, the temperature of the reaction mixture is cycled through a denaturing region, a primer annealing region, and a reaction region. A machine specifically adapted for use with a thermostable enzyme was developed and manufactured by Hoffmann-La Roche Inc. and is commercially available from Perkin Elmer (Norwalk, Conn.).

Those skilled in the art will also be aware of the problem of contamination of a PCR by the amplified nucleic acid from previous reactions. Methods to reduce this problem are provided in PCT patent publication No. WO 92/0184 and U.S. patent application Ser. No. 880,629, May 8, 1992, now abandoned each of which is incorporated herein by reference. The methods allow the enzymatic degradation of any amplified DNA from previous reactions. The PCR amplification is carried out in the presence of dUTP instead of dTTP. The resulting double stranded uracil containing product is subject to degradation by uracil N-glycosylase (UNG), whereas normal thymine-containing DNA is not degraded by UNG. Adding UNG to the amplification reaction mixture before the amplification is started degrades all uracil containing DNA that might serve as target. Because the only source of uracil containing DNA is the amplified product of a previous reaction, this method effectively sterilizes the reaction mixture, eliminating the problem of contamination from previous reactions (carryover). UNG is rendered temporarily inactive by heat, so the denaturation steps in the amplification procedure also serve to inactivate the UNG. New amplification products, therefore, though incorporating uracil, are formed in an UNG-free environment and are not degraded.

In general, it is preferred but not essential that the DNA polymerase is added to the PCR reaction mixture after both the primer and template are added. Alternatively, for example, the enzyme and primer are added last or the PCR buffer or template plus buffer are added last. It is generally desirable that at least one component that is essential for polymerization not be present until such time as the primer and template are both present, and the enzyme can bind to and extend the desired primer/template substrate (see U.S. Pat. No. 5,411,876, which is incorporated herein by reference). This method, termed "hot start," improves specificity and minimizes the formation of "primer-dimer."

Sequence specific probe hybridization is an important step in successful performance of the present methods. The sequence specific oligonucleotide probes of the present invention hybridize specifically with a particular segment of the genome of human *P. carinii* and have destabilizing mismatches with the sequences from other strains and other organisms. Stringent hybridization conditions may be chosen so that the probes hybridize specifically only to exactly complementary sequences. Detection of the amplified product utilizes this sequence specific hybridization to insure that only the correct amplified target is detected, decreasing the chance of a false positive caused by the presence of homologous sequences from related organisms.

The assay methods for detecting hybrids formed between SSO probes and nucleic acid sequences can require that the probes contain additional features in addition to the hybridizing region. In the dot blot format, for example, the probes are typically labeled. If the probe is first immobilized, as in the "reverse" dot blot format described below, the probe can also contain long stretches of poly-dT that can be fixed to a nylon support by irradiation, a technique described in more detail in PCT Patent Publication No. WO 89/11548, incorporated herein by reference.

The probes of the invention can be synthesized and labeled using the techniques described above for synthesizing oligonucleotides. For example, the probe may be labeled at the 5'-end with $^{32}$P by incubating the probe with $^{32}$P-ATP and kinase. A suitable non-radioactive label for SSO probes is horseradish peroxidase (HRP). Methods for preparing and detecting probes containing this label are described in U.S. Pat. Nos. 4,914,210 and 4,962,029, each of which is incorporated herein by reference. For additional information on the use of such labeled probes, see U.S. Pat. No. 4,789,630; Saiki et al., 1988, *N. Eng. J. Med.* 319:537–541; and Bugawan et al., 1988, *Bio/Technology* 6:943–947, each of which is incorporated herein by reference. Useful chromogens include red leuco dye and 3,3',5,5'-tetramethylbenzidine (TMB). Helmuth, *PCR Protocols,* San Diego, Calif., Academic Press, Inc., 1990, pp. 119–128, describes procedures for non-isotopic detection of PCR products and is incorporated herein by reference.

The probes of the invention can be used to determine if nucleic acid sequences are present in a sample by determining if the probes bind to the sequences present in the sample. Suitable assay methods for purposes of the present invention to detect hybrids formed between probes and nucleic acid sequences in a sample are known in the art. For example, the detection can be accomplished using a dot blot format, as described in the Example 4. In the dot blot format, the unlabeled amplified sample is bound to a solid support, such as a membrane, the membrane incubated with labeled probe under suitable hybridization conditions, the unhybridized probe removed by washing, and the filter monitored for the presence of bound probe. When multiple samples are analyzed a single probe, such as when samples are screened for the presence of *P. carinii* nucleic acid, the dot blot format is preferred.

An alternate method is quite useful when large numbers of different probes are to be used. This method is a "reverse" dot blot, in which the amplified sequence contains a label, and the probe is bound to the solid support. In this format, the unlabeled probes are bound to the membrane and exposed to the labeled sample under appropriately stringent hybridization conditions. Unhybridized labeled sample is then removed by washing under suitably stringent conditions, and the filter is then monitored for the presence of bound sequences.

Alternatively, it may be desirable to use a detection method having a plurality of probe hybridization sites or wells. For example, a solid support such as a microliter plate is particularly useful in large scale clinical applications of the present methods. Copending U.S. patent application Ser. No. 695,072, filed May 3, 1991, and U.S. Pat. No. 5,232,829, incorporated herein by reference, describe preferred methods for hybridization/capture of PCR amplified DNA or solid supports. In one embodiment of those methods the amplified target DNA is labeled (e.g., with biotin) during amplification in the PCR reaction. The labeled DNA is specifically captured by hybridization of PCR product to a target-specific oligonucleotide capture probe that has been bound to the microliter plate well. The bound product is suitably detected according to the type of label used. For example, if biotin is used as a label, avidin HRP complex is added and is reacted with either (a) hydrogen peroxide substrate and O-phenylene diamine (OPD) chromogen or (b) hydrogen peroxide substrate and tetramethylbenzidine chromogen (TMB). A colorimetric signal develops, allowing for the quantitative detection of the PCR amplified DNA.

Another suitable assay system is described in U.S. Pat. No. 5,210,015, incorporated herein by reference, in which a labeled probe is added during the PCR amplification process. Any probe that hybridizes to target DNA during each synthesis step is degraded by the 5' to 3' exonuclease activity of the polymerase used to catalyze primer extension. The degradation product from the probe is then detected. Thus, the presence of the degradation product indicates that the hybridization between the probe and the target DNA occurred.

The present invention also relates to kits, multicontainer units comprising the primers and probes of the invention. A useful kit can contain SSO probes for detecting *P. carinii* nucleic acid. In some cases, the SSO probes may be fixed to an appropriate support membrane. The kit can also contain primers for PCR amplification. Other optional components of the kit include, for example, reverse-transcriptase or DNA polymerase, the substrate nucleoside triphosphates, means used to label (for example, an avidin-enzyme conjugate and enzyme substrate an, chromogen if the label is biotin) or detect label, and the appropriate buffers for PCR, reverse transcription, or hybridization reactions. In addition to the above components, the kit can also contain instructions for carrying out amplification and detection methods of the invention.

In a preferred embodiment of the invention; kits for detecting *P. carinii* may also include positive and negative controls. Preferably a positive control includes a nucleic acid sequence that is amplifiable using the same primer pair used to amplify *P. carinii* nucleic acids in a test sample. Methods for using a positive control, wherein both the target that may or may not be present, and the positive control, use the same primer pair are described in U.S. Pat. No. 5,219,727, incorporated herein by reference. Preferably the positive control is designed so that the product DNA is of a discrete size readily distinguishable from the size of the target. Example 8, below, describes the construction of a positive control nucleic acid.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Sample Preparation

The following protocols are for use with concentrated, liquified, decontaminated sputum or bronchial alveolar lavage specimens. Specimens are prepared using the Sputolysin Stat-Pak kit from Behring Diagnostics (Westwood, Mass.).

Method A

A 100 µl volume of liquified induced sputum is suspended in 200 µl of buffer (10 mM Tris, pH 8.3; 1 mM EDTA, pH 8; 0.5% SDS; 100 µg/ml proteinase K) and incubated at 56° C. for two hours. The sample is then extracted with Phenol/$CHCl_3$, extracted with $CHCl_3$, ethanol precipitated, and centrifuged. Finally, the pellet is dissolved in 100 µl TE (Tris/EDTA as described in Sambrook et al., 1985, supra).

Method B

This sample preparation protocol uses three solutions: Wash solution (10 mM Tris-HCl, 1 mM EDTA, 1% weight/volume Triton X-100 (Fisher (Springfield, N.J.)), 0.05% $NaN_3$, pH 8.0 at 25° C.), Lysis solution (0.1N NaOH, 1% weight/volume Triton X-100, 1 mM EDTA, 0.05% $NAN_3$), and Neutralization buffer (200 mM Tris-HCl, 8 mM $MgCl_2$, 0.05% $NaN_3$, pH 7.5 at 25° C.). Preferably, sample preparation is carried out in 1.5 ml screw-cap tubes (Sarstedt (Newton, N.C.)).

Add 0.5 ml of wash solution to 100 µl of sample and vortex for 5 seconds at maximum speed. Centrifuge for 10 minutes at a minimum of 12,500×g in a micro-centrifuge at room temperature.

Aspirate the supernatant, add 50 µl of Lysis solution, and vortex for 5 seconds at maximum speed. Incubate the specimens at 55° C. for 45 minutes in an Eppendorf Thermomixer (Brinkman Model 5436, VWR (Piscataway, N.J.)) at maximum mixing speed.

Add 50 µl of Neutralization solution to each tube containing 50 µl of Lysis solution and vortex for 5 seconds at maximum speed. Pulse centrifuge at maximum speed for 5 seconds to fully recover the neutralized sample.

A 50 µl volume of neutralized sample is used in each amplification reaction, as described below. Store unused sample at −80° C.

EXAMPLE 2

Amplification of Pneumocystis carinii DNA

PCR amplifications are carried out in a total reaction volume of 100 µl. A 50 µl DNA sample is added to 50 µl of reaction mixture containing the following reagents:

1 µl of each primer (in a 50 µM solution),

4 µl of 10 mM dNTP mix (or, equivalently, 1 µl of each dNTP in a 10 mM solution), 10 µl 10X PCR buffer (500 mM KCl, 100 mM Tris-HCl, pH 8.3), 10 µl 25 mM MgCl$_2$, 0.6 µl Taq polymerase (developed and manufactured by Hoffmann-La Roche Inc. and commercially available from Perkin Elmer (Norwalk, Conn.)) @5 U/µl, 2 µl UNG (developed and manufactured by Hoffmann-La Roche Inc. and commercially available from Perkin Elmer (Norwalk, Conn.)) @1 U/µl, 20 µl 50% Glycerol, and 1.4 µl H$_2$O.

If sample preparation method B of Example 1 is used, the KCl is omitted from the PCR buffer. The DNA is amplified in a TC 9600 Thermal Cycler (developed and manufactured by Hoffmann-La Roche Inc. and commercially available from Perkin Elmer (Norwalk, Conn.)). The Thermal Cycler is programmed to incubate the sample at 50° C. for 2 minutes, followed by 37 cycles of denaturation, primer annealing, and primer extension: two cycles of 98° C. for 20 seconds, 62° C. for 20 seconds, and 72° C. for 45 seconds; followed by 35 cycles of 94° C. for 20 seconds, 62° C. for 20 seconds, and 72° C. for 45 seconds. The Thermal Cycler is programmed to soak the samples at 72° C. for 5 minutes after the last cycle to ensure that the final extension is complete and to keep the UNG enzyme inactive. The amplification products are then analyzed immediately by gel electrophoresis and/or dot blot hybridization. If analysis by gel electrophoresis is to be done, about 10 µl of 10X sample buffer (0.25% xylene cyanol, 0.25% bromophenol blue, 25% Ficoll) are added and the Taq polymerase is inactivated with 100 µl of chloroform. The electrophoretic analysis of DNA is well known in the art and described in, e.g., Sambrook et al., 1985, supra.

EXAMPLE 3

Dot Blot Format

In the dot blot format a small portion of the amplified DNA is denatured, applied to a nylon filter, and immobilized as described below. The filter is then immersed in a probe solution to allow hybridization to the labeled probes. Probes can be radioactively labeled, but probes covalently conjugated to horseradish peroxidase (HRP) can also be used to provide a means of nonisotopic detection in the presence of a chromogenic or chemiluminescent substrate. This format is suitable for the analysis a large number of samples. Many samples can be immobilized onto discrete locations of a single solid support and exposed to the labeled probe simultaneously by immersion of the support in a probe solution.

The amplification is carried out as in Example 2. The PCR product is then denatured by treatment with alkali. To 5 µl of PCR product is added 5 µl of 0.5M EDTA, pH 8.0, 8 µl of 5N NaOH, and 82 µl of H$_2$O. The mixture is allowed to stand at room temperature for 10 minutes to complete denaturation.

BioDyne™ B nylon filters (Pall Corp., Glen Cove, N.Y.) are prepared by soaking in H$_2$O for 5 to 10 minutes and further rinsing with 200 µl of H$_2$O after the dot-blot manifold (Bio-Dot™ from Bio-Rad, Richmond, Calif.) has been set up. Following denaturation, 100 µl of the sample mixture is applied under vacuum to the nylon membrane using the dot blot apparatus. Each well is then rinsed with 200 µl of 0.4N NaOH, then rinsed briefly with 2X SSC, and air dried until no pools of liquid are left. The DNA is immobilized and crosslinked to the nylon filter by ultraviolet irradiation at a flux of 1200 mJ/cm$^2$ with a Stratalinker™ (Stratagene, La Jolla, Calif.) UV light box (at the "autocrosslink" setting).

Filters are "prehybridized" by soaking in the hybridization buffer (0.5X SSC, 5X Denhardt's solution, 0.1% SDS, 50 µg/ml of herring sperm DNA) in heat sealable bags at 60° C. (air shaker) for at least 30 minutes. If radioactively labeled probes are used, the buffer is then replaced with an equal amount of the same solution containing 1×10$^6$ cpm probe, and the filter is allowed to hybridize between 2 hours and overnight at 60° C.

After hybridization, filters are washed three times in 2X SSC/0.1% SDS; twice for 20 minutes at room temperature, and then once for twenty minutes at the high stringency temperature of 71° C. in a shaking water bath. The filters are then blotter dry, wrapped in plastic wrap, and exposed to X-ray film at −70° C. with one or two intensifying screens.

An alternate method of visualization is to hybridize with horseradish peroxidase conjugated oligonucleotide probes, prepared as described by Levenson and Chang, 1989, in *PCR Protocols: A Guide to Methods and Applications,* (Innis et al., eds., Academic Press. San Diego) pages 92–112, and Saiki et al., 1988, *N. Eng. J. Med.* 319:537–541, both of which are incorporated herein by reference. Hybridization is carried out with 2 pmoles of HRP-SSO probe per 5 ml of hybridization solution.

After washing, filters to be developed with a chromogenic dye substrate are rinsed in 100 mM sodium citrate, pH 5.0, then placed in 100 mM sodium citrate, pH 5.0, containing 0.1 mg/ml of 3,3',5,5'-tetramethylbenzidine per milliliter (Fluka, Ronkonkoma, N.Y.) and 0.0015 percent hydrogen peroxide, and incubated with gentle agitation for 10 to 30 minutes at room temperature. Developed filters are rinsed in water and immediately photographed. The TMB detection system is prepared and used substantially as described in AmpliType® DQalpha DNA typing kit developed and manufactured by Hoffmann-La Roche and available through Perkin Elmer. In another embodiment, filters are developed with the chemiluminescent detection system (ECL; Amersham, Arlington Heights, Ill.). Filters are rinsed in PBS for 5 minutes and placed in the ECL solution for 1 minute with gentle agitation. Filters are then exposed to X-ray film at room temperature for 1 to 5 minutes.

EXAMPLE 4

Reverse Dot Blot Format

An alternate hybridization format is the reverse dot blot format in which the probes are fixed to discrete locations on a membrane and then the entire membrane is immersed in a solution containing the amplified target DNA to allow hybridization to the membrane-bound probes. The reverse dot blot process is described in Saiki et al., 1989, *Proc. Natl. Acad. Sci.* 86:6230–6234; and in the AmpliType® DQalpha DNA typing kit developed and manufactured by Hoffmann-La Roche Inc. and available through Perkin Elmer, each of which is incorporated herein by reference. The amplification primers are biotinylated, as described in Levenson and Chang, 1989, supra, so that any amplified DNA that hybridizes to the membrane bound probes can be easily detected.

In one embodiment, target sequences are amplified using biotinylated primers and the PCR product is then hybridized to membrane-bound probe. Detection is carried out by reacting streptavidin conjugated horseradish peroxidase:(SA-HRP) with the amplified DNA hybridized to the fixed probe. The HRP thus becomes bound, through the SA-biotin interaction, to the amplified DNA and can be used to generate a signal by a variety of well known means, such as the generation of a colored compound, e.g., by the oxidation of tetramethylbenzidine (see U.S. Pat. No. 4,789,630, incorporated herein by reference).

Although the probe can be fixed to the membrane by any means, a preferred method involves "tailing" an oligonucleotide probe's hybridizing region with a much longer sequence of poly-dT. The resulting poly-dT "tail" can then be reacted with amine groups on a nylon membrane to fix the probe covalently to the membrane. This reaction can be facilitated by UV irradiation.

Terminal deoxyribonucleotidyl transferase (TdT, Ratliff Biochemicals; for the reactions below assume a concentration of abut 120 Units/µl, which is 100 pmole/µl) can be used to cream a poly-dT tail on a probe, although one can also synthesize the tailed probe on a commercially available DNA synthesizer. When one uses a DNA synthesizer to make the tailed probe, however, one should place the tail on the 5' end of the probe, so that undesired premature chain termination occurs primarily in the tail region.

TdT reactions should be carried out in a volume of about 100 µl containing 1X TdT salts, 200 pmole of oligonucleotide, 800 µM DTT, and 60 units of TdT. 10X TdT salts is 1,000 mM K-cacodylate, 10 mM $CoCl_2$, 2 mM dithiothreitol, 250 mM Tris-Cl, pH 7.6, and is prepared as described by Roychoudhury and Wu, *Meth. Enzymol.* 65: 43–62, incorporated herein by reference. A 10X stock solution of 8 mM dTTP can be prepared (neutralized to pH 7 with NaOH) for convenience.

The TdT reaction should be carried out at 37° C. for two hours and then stopped by the addition of 100 µl of 10 mM EDTA, pH 8. The final concentration of tailed oligonucleotide is 1 µM (1 pmole/µl), and the length of the homopolymer tail is about 400 residues. Tail length can be changed by adjusting the molar ratio of dTTP to oligonucleotide. The tailed probes can be stored at −20° C. until use.

The nylon membrane preferred for the reverse dot blot format is the BioDyne™ B nylon membrane, 0.45 micron pore size, manufactured by Pall and also marketed by ICN as the BioTrans™ nylon membrane. The probes can be spotted onto the membrane very conveniently with the Bio-Dot™ dot blot apparatus manufactured by Bio-Rad. Each probe is spotted onto a unique, discrete location on the membrane. About 2 to 10 picomoles of each tailed probe is premixed with 50 to 100 µl of TE buffer before application to the dot blot apparatus. After dot blotting, the membrane is briefly placed on absorbent paper to draw off excess liquid. The membrane is then placed inside a UV light box, such as the Stratalinker™ light box manufactured by Stratagene, La Jolla, Calif., and exposed to 50 to 60 millijoules/$cm^2$ of flux at 254 nm to fix the tailed probe to the nylon membrane. After a brief rinse (for about 15 minutes in hybridization solution) to remove unbound probe, the membrane is then ready for hybridization with biotinylated PCR product.

Amplified PCR products are denatured by heating to 95° C. for 3 to 10 minutes, and 40 µl of the denatured PCR product are added to each probe panel for hybridization. Hybridization is carried out at 57° C. for 20 minutes in a shaking water bath in a hybridization buffer composed of 0.5X SSC, 0.25% SDS, and 5X Denhardt's solution. The hybridization buffer is replaced with 3 ml of a solution consisting of 25 µl of SA-HRP, developed and manufactured by Hoffmann-La Roche Inc. and commercially available from Perkin Elmer (Norwalk, Conn.), in 3.1 ml of hybridization buffer, and incubated for 20 minutes at 57° C. in a shaking water bath.

Washing is carried out in a wash buffer of 2X SSC and 0.1% SDS. After a brief rinse of the membrane in 10 ml of wash buffer, a 12 minute stringent wash in 10 ml of buffer is done at 57° C. Another 5 minute room temperature wash is then carried out, followed by a 5 minute wash in 10 ml of 0.1M sodium citrate, pH 5.0.

Chromogen binding is carried out in 5 ml of chromogen solution consisting of 5 ml of 0.1M sodium citrate, 5 µl of 3% hydrogen peroxide, and 0.25 ml of chromogen (TMB, developed and manufactured by Hoffmann-La Roche Inc. and commercially available from Perkin Elmer (Norwalk, Conn.)) for 25–30 minutes at room temperature. Three 10 minute washes in distilled water are carried out at room temperature. A post-wash of 1X PBS at room temperature for 30 minutes can enhance signal quality. During steps in which chromogen is present, the membrane should be shielded from light by an aluminum foil covering. The developed membrane should be photographed for a permanent record.

EXAMPLE 5

Microwell Plate Assay for the Detection of *Pneumocystis carinii*

In this embodiment of the invention, the probe is fixed to a well of a microwell plate. The amplified target DNA is hybridized to the bound probe as described above. As in the previous example, the amplification primers are biotinylated to allow detection of amplified DNA that hybridizes to the bound probes.

The probes are immobilized on the plastic surface of a microwell plate as follows. One hundred µl of a solution of 1M $CH_3COONH_4$ containing probe at a concentration of 0.5 nanogram/µl are added into each well of a microwell plate. The plate is incubated at 37° C. for 10 to 20 hours (overnight) and then rinsed with PBS/EDTA (PBS is 2.68 mM KCl, 137 mM NaCl, 1.47 mM $KH_2PO_4$, and 8.03 mM $Na_2HPO_4$). Alternatively, probes conjugated to bovine serum albumin (BSA) are allowed to adsorb to the plastic surface of the individual wells. The wells are then blocked with protein, such as BSA. Preferably, 96 well plates available from Corning are used with either immobilization method. Amplification is carried out as described above. One hundred microliters of denaturation solution (0.4M NaOH; 80 mM EDTA and 0.005% Thymol blue) are added to each PCR tube. A new pipette tip is used for each tube. In one embodiment, detection may not be performed immediately, in which case the PCR tubes are storied overnight at 2° C. to 8° C. Because denatured amplification reactions become viscous upon storage at 2° C. to 8° C., tubes are briefly warmed at 25° C. to 30° C. prior to opening to make pipette easy.

The appropriate number of eight well microwell plate strips (minimally 2 strips) are removed and set into the microwell plate frame. One hundred µl of hybridization/neutralization buffer was pipetted into each well of the microwell plate. Hybridization/neutralization buffer contains 3M NaSCN, 80 mM NaH$_2$PO$_4$, 10 mM NaH$_2$PO$_4$, and 0.125% Tween 20. Before use the pH is checked to be 5.0±0.2.

Using plugged tips with a multi channel pipetter, 25 μl of the denatured amplification reaction from each PCR tube in the tray is pipetted to the corresponding well position in the microwell plate. The plate is covered with the microwell plate lid and gently tapped on the side 10 to 15 times. Wells in which proper reagent pipeting has been done will turn light yellow in color. No change or only a slight change in blue color indicates that excess amplified product has been added. This will not affect the assay results, however. The addition of excess amplified product will increase positive OD values but negative OD values will not be affected. The plate is incubated for 60 minutes at 37° C. to allow hybridization. The hybridization/neutralization buffer is removed and replaced with fresh hybridization/neutralization buffer, and the plate is incubated for an additional 15 minutes at 37° C.

Following incubation the plate is washed five times with a 1X PCR wash buffer. A 10X concentrate of PCR wash buffer contains 9.94 grams per liter of sodium phosphate dibasic, 4.41 grams per liter sodium phosphate (monobasic), 3.722 grams per liter EDTA, 87.66 grams per liter sodium chloride, 13.7 grams per liter of Tween 20, and 10 grams per liter of Pro Clin 300 (Rohm and Haas, Philadelphia, Pa.). The pH of the solution is adjusted with phosphoric acid (pH 6.5–7.1 is preferred). Washing of the plate may be performed manually or with an automated microwell plate washer programmed accordingly.

For manual washing the contents of the plate are emptied and tapped dry. Three hundred μl of wash solution are added to .each well in the plate being tested, and the plate is allowed to dry for 15 to 30 seconds. The plate is again emptied and tapped dry. This wash process is repeated four additional times.

For an automated microplate washer, the following procedure is used. The contents of the wells are aspirated. The washer is programmed to add 350 microliters of working wash solution to each well in the plate being tested, soak for 30 seconds, and aspirate. The steps are repeated four additional times. The plate is then tapped dry.

Avidin-HRP conjugate is prepared as follows. A diluent is prepared that contains; 0.25% Emulsit 25 (DKS International, Inc., Tokyo, Japan); 1.0% Kathon CG (Rohm and Haas, Philadelphia, Pa.); 0.1% phenol; 1.0% bovine gamma globulin. The pH of the diluent solution is adjusted to 7.3 with concentrated HCl. To this diluent, 10 nM of conjugated avidin (Vector Labs, Burlingame, Calif.) is added. One hundred μl of avidin-HRP conjugate is added to each well in the plate being tested. The plate is then covered and incubated 50 minutes at 37° C. and again washed as described above.

A working substrate is prepared by mixing 2.0 ml of substrate A (3 mM hydrogen peroxide, 6.5 mM citrate, and 0.1% Kathon CG) and 0.5 ml of Substrate B (4.2 mM 3,3',5,5' tetramethylbenzidine and 40% dimethylformamide) for each multiple of two 8 well microwell plate strips (16 tests). The working substrate is prepared no more than three hours before use and stored away from direct sunlight. One hundred μl of working substrate (substrate A and B mixture) are added to each well of the plate being tested. The plate is then covered and incubated in the dark for 10 minutes at room temperature (20° C. to 25° C.).

One hundred μl of Stop Reagent (5% H$_2$SO$_4$) is added to each well being tested. The absorbance of each well of 450 nM is read within one hour of adding the Stop Reagent.

EXAMPLE 6

Amplification of *Pneumocystis carinii* 18S rRNA

The 18S rRNA can be amplified by first creating cDNA by reverse transcription and amplifying the cDNA. The same primers are used as in Example 2, above. In this example, both the high temperature reverse transcription and the PCR amplification are carried out with the thermostable Tth polymerase.

The reverse transcription is carried out in a volume of 20 μl containing the following components: 8 μl of H$_2$O, 2 μl of 10X RT reaction buffer (100 mM Tris-HCl, pH 8.3, and 900 mM KCl), 2 μl of 10 mM MnCl$_2$, 2 μl of dNTP solution (2 mM each of dATP, dCTP, dGTP, and dTTP in H$_2$O, pH 7.0), 2 μl of the "downstream" primer (7.5 mM in H$_2$O), 2 μl of 0.18 μM Tth polymerase in 1X storage buffer (20 mM Tris-HCl, pH 7.5, 100 mM KCl, 0.1 mM EDTA, 1 mM DTT, 0.2% Tween 20 (Pierce (Rockford, Ill.)), 50% (volume/volume) glycerol), and 2 μl of template RNA solution (<250 ng in 10 mM Tris-HCl and 1 mM EDTA). All solutions not containing Tris are treated with diethylpyrocarbonate (DEPC) to remove any contaminating ribonuclease as described on page 190 of Maniatis et al., 1982, *Molecular Cloning, a Laboratory Manual* (Cold Springs Harbor Laboratory, New York), incorporated herein by reference. The reverse transcription is carried out at 72° C. for 5 minutes in a thermocycler. The reaction is stopped by cooling the reaction to 4° C. with ice.

The PCR amplification is performed with the following reagents added: 2 μl of the remaining primer (7.5 mM in H$_2$O), 2 μl of dNTP solution (10 mM each of dATP, dCTP, dGTP, and dTTP in H$_2$O, pH 7.0), 8 μl of 10X PCR reaction buffer (100 mM Tris-HCl, pH 8.3, 1 mM KCl, 18.75 mM MgCl$_2$, 7.5 mM EGTA, and 50% (volume/volume) glycerol), and 68 μl DEPC treated H$_2$O. The nucleic acid is amplified in a Perkin Elmer Thermal Cycler with the same thermal profile as in Example 2. The amplified product is analyzed as described in the prior examples.

EXAMPLE 7

Sequencing the 18S rRNA Gene

DNA sequence was obtained for 951 base pairs of the 18s rRNA gene from three different clinical isolates. As described below, a fragment of the 18S rRNA gene of *P. carinii* was generated by a hemi-nested PCR amplification and sequenced by a standard technique. The three samples consisted of DNA extracted from human clinical specimens which were positive for *P. carinii* by microscopy. Samples were prepared as described in Kitada et al., 1991, *J. Clin. Microbiol.* 29(9):1985–1990.

The first amplification used primers PC23 (SEQ ID No. 16) and TW8 (SEQ ID No. 14) to amplify a region of the 18S rRNA gene approximately 1200 base pairs in length. The hybridizing regions of primers PC23 (SEQ ID No. 16) and TW8 (SEQ ID No. 14), a nonspecific fungal primer, are provided below. Amplification was carried out essentially as described in Example 2, but using the modified conditions described below.

The initial PCR amplification using primers PC23 (SEQ ID No. 16) and TW8 (SEQ ID No. 14) was carried out in a total reaction volume of 100 μl containing 5 μl of sample and 95 μl of a reaction mixture containing the following reagents:

1 μl of each primer (in a 50 μM solution), 2.5 µl of 10 mM dNTP mix (in equal ratio of each dNTP)

10 µl 10X PCR buffer (500 mM KCl, 100 mM Tris-HCl, pH 8.3, 15 mM

MgCl$_2$, 0.01% gelatin), 0.5 µl Taq polymerase (developed and manufactured by Hoffmann-La Roche Inc. and commercially available from Perkin Elmer (Norwalk, Conn.)) @5 U/µl, 4 µl 50% Glycerol, and 76 µl H$_2$O.

The reaction mixture was overlaid with 50 µl of oil. The temperature profile for the amplification was 95° C. for 5 minutes; 30 cycles of 95° C. for 1 minute, 55° C. for 1 minute, and 72° C. for 2 minutes; 72° C. for 10 minutes; and soak at 15° C.

The second amplification using primers FP1 (SEQ ID No. 15) and TW8 (SEQ ID No. 14) were carried out to reamplify 5 µl of diluted amplification product from the first PCR (using primers PC23 [SEQ ID No. 16] and TW8 [SEQ ID No. 14]). Primer FP1 (SEQ ID No. 15), a nonspecific fungal primer whose hybridizing sequence is provided below, hybridizes downstream of PC23 (SEQ ID No. 16) and the resulting amplified product is approximately 970 base pairs in length. The initial amplification product from the first PCR was diluted by adding 495 µl H$_2$O to 5 µl product. The second PCR amplification was carried out in a total reaction volume of 100 µl containing 5 µl of diluted sample and 95 µl of a reaction mixture containing the following reagents:

1 µl of each primer (in a 50 µM solution), 2.5 µl of 10 mM dUNTP mix (in equal ratio of each dNTP)

10 µl 10X PCR buffer (500 mM KCl, 100 mM Tris-HCl, pH 8.3, 15 mM

MgCl$_2$, 0.01% gelatin), 0.5 µl Taq polymerase (developed and manufactured by Hoffmann-La Roche Inc. and commercially available from Perkin Elmer (Norwalk, Conn.)) @5 U/µl, 10 µl 50% Glycerol, and 70 µl H$_2$O.

The reaction mixture was overlaid with 50 µl of oil. The temperature profile for the second amplification was 95° C. for 5 minutes; 30 cycles of 95° C. for 1 minute, 55° C. for 1 minute, and 72° C. for 1 minute; 72° C. for 10 minutes; and soak at 15° C.

Before sequencing, the amplified product from the second PCR was purified using a Centricon 100 (Amicon (Danvers, Mass.)) size exclusion column. The purified amplification product was sequenced using the dye-terminator cycle sequencing procedure (Applied Biosystems, Inc. (Foster City, Calif.)). Identical sequences were obtained for the three isolates (see Table 1).

EXAMPLE 8

The Construction of a Positive Control Vector Useful in Methods for the Amplification and Detection of Pneumocystis carinii Nucleic Acids A vector containing a region of the 18S rRNA gene of *P. carinii* was created by inserting a gene fragment generated by the hemi-nested PCR amplification described in Example 7, above, into the vector pUC19 (ATCC 37254) using standard cloning techniques well known in the art (see Sambrook et al., 1985, supra; and the *Promega Protocols and Applications Guide*, available commercially from Promega, Madison, Wis., and incorporated herein by reference).

The amplification product from Example 7, above, was treated with Klenow fragment to insure that the ends were blunt (incubate 90 µl of reaction product with 9.5 µl 50 mM MgCl$_2$ and 0.5 µl Klenow fragment @5 U/µl at room temperature for 20 minutes). The reaction products (100 µl) were transferred to a new 0.5 ml tube and ethanol precipitated (add 10 µl 3M NaOAc and 220 µl ETOH, mix by inversion, incubated at room temperature for 10 minutes, and spun at high speed for 15 minutes in an Eppendoff microfuge). The pellet was resuspended in a solution containing 15 µl H$_2$O, 2 µl of 10 X kinase buffer (500 mM Tds, pH 8.0, 100 mM MgCl$_2$, 50 mM DTT), 2 µl dATP @10 µM, and 1 µl T4 polynucleotide kinase (Boehringer-Mannheim), incubated at 37° C. for 30 minutes, and then incubated at 68° C. for 10 minutes to inactivate the kinase.

A 15 µl volume of the amplification product was purified using a Centricon 100 (Amicon, Danvers, Mass.) size exclusion column and about 40 µl of purified product were ethanol precipitated (add 4 µl 3M NaOAc and 88 µl ETOH, mix by inversion, incubated at room temperature for 10 minutes, and spun at high speed for 15 minutes in an Eppendoff microfuge). The pellet was resuspended in 15 µl TE.

The vector pUC19 (ATCC 37254) was linearized by digestion with restriction endonuclease Hinc II and dephosphorylated by treatment with calf intestine phosphatase (see Sambrook et at., 1985, supra). The prepared amplification products were ligated to the vector using T4 ligase under standard conditions (see Sambrook et al., 1985, supra).

The ligated DNA was transformed into competent *E. coli* (DH5alpha from Life Technologies, Inc., Grand Island, N.Y.). The cells were streaked onto selection plates to identify transformed cells using standard protocols (see Sambrook et al., 1985, supra).

Colonies incorporating plasmids that contain the desired insert were identified by PCR amplification using M13 primers (Stratagene, La Jolla, Calif.), which hybridize to the vector in regions flanking the insert. Transformant bacterial

TABLE 4

| Primer | Sequence Listing | Sequence |
| --- | --- | --- |
| TW8 | SEQ ID No: 14 | 5'-TCCGCAGGTTCACCTACGGA |
| FP1 | SEQ ID No: 15 | 5'-GTGGTTCTATTTTGTTGGTTTCTA |
| PC23 | SEQ ID No: 16 | 5'-TGGTTGCCTGGTCCTCCGAAG | colonies were resuspended in 0.5 ml TE buffer. Amplifications were carried out in 100 µl volumes, 50 µl sample and 50 µl reaction mix (36.2 µl H$_2$O, 0.4 µl each primer [@25 mM], 10 µl 10 X reaction buffer [see Example 7], 2.5 µl 10 mM dNTP mix, 0.5 µl Taq polymerase [developed and manufactured by Hoffmann-La Roche Inc. and commercially available from Perkin Elmer, Norwalk, Conn.]@5 U/µl). The amplification temperature profile consisted of 95° C. for 5 minutes; 30 cycles of 95° C. for 1 minute, 55° C. for 1 minute, and 72° C. for 1 minute; a 5 minute extension at 72° C.; and soaked at 15° C. The amplification product was analyzed using a 2.5% Nusieve+0.5% agarose gel.

Two plasmid vectors containing the 18S rRNA gene insert were identified, designated pSSP1 and pJN01. The plasmids differ in the orientation of the insert. Following identification, the plasmids were grown, purified, characterized, and quantitated by standard methods.

The two plasmids served as amplification templates with similar efficiencies. Circular and linearized (digested with EcoRI and HindIII) pSSP1 were compared as amplification templates in three diluents, 1 ng/µl human placental DNA, 1 ng/µl calf thymus DNA and 1X TE. Amplifications were as described in Example 2, above. Linearized plasmid produced approximately 10-fold greater signal than circular plasmid. Amplification of 10 copies of the linearized plasmid was visible on an ethidium bromide-stained agarose gel. Specific amplification appeared to be equal in the three diluents.

EXAMPLE 9

The Use of Positive Control Plasmid

One use of the positive control plasmid is to monitor the efficiency of amplification in any specific experiment. In such applications, serial dilutions of the positive control plasmid are made. Known copy numbers of the plasmid can be used as templates in amplification reactions. The lowest number of plasmid DNA molecules that can be amplified gives a measurement of the efficiency of the amplification reaction. Another use of the positive control plasmid is to generate products which can be used to monitor the efficiency with which the sequence specific probes detect P. carinii DNA. Amplification products generated as above can serve as substrate in hybridization reaction. Generation of the appropriate hybridization signals allows for an assessment of how well the probes are able to detect P. carinii DNA.

EXAMPLE 10

Probe Comparisons

Three probes, PC102 (SEQ ID No. 8), PC104 (SEQ IN No. 9), and PC110 (SEQ.ID No. 12), and their complements were compared in a microwell hybridization assay essentially as described in Example 5, above. The microwell plates were coated passively at 50 ng/well of probe. Amplification products from amplifications performed essentially as described in Example 2, above, using primers PC41 (SEQ ID No. 4) and PC22 (SEQ ID No. 5) on samples containing pSSP1, were pooled, serially diluted, denatured and added to the coated plates. The results are shown in FIG. 1. Designations of the complements in FIG. 1 are as follows: PC101 is the complement of PC102 (SEQ ID No. 8), PC103 is the complement of PC104 (SEQ ID No. 9), and PC109 is the complement of PC 110 (SEQ ID No. 12). All probes were able to capture PC41 (SEQ ID No. 4)/PC22 (SEQ ID No. 5) PCR product without excessive background signals, but PC102 (SEQ ID No. 8) and PC104 (SEQ ID No. 9) showed the strongest specific signals.

EXAMPLE 11

Analytical Sensitivity

Figure 2:
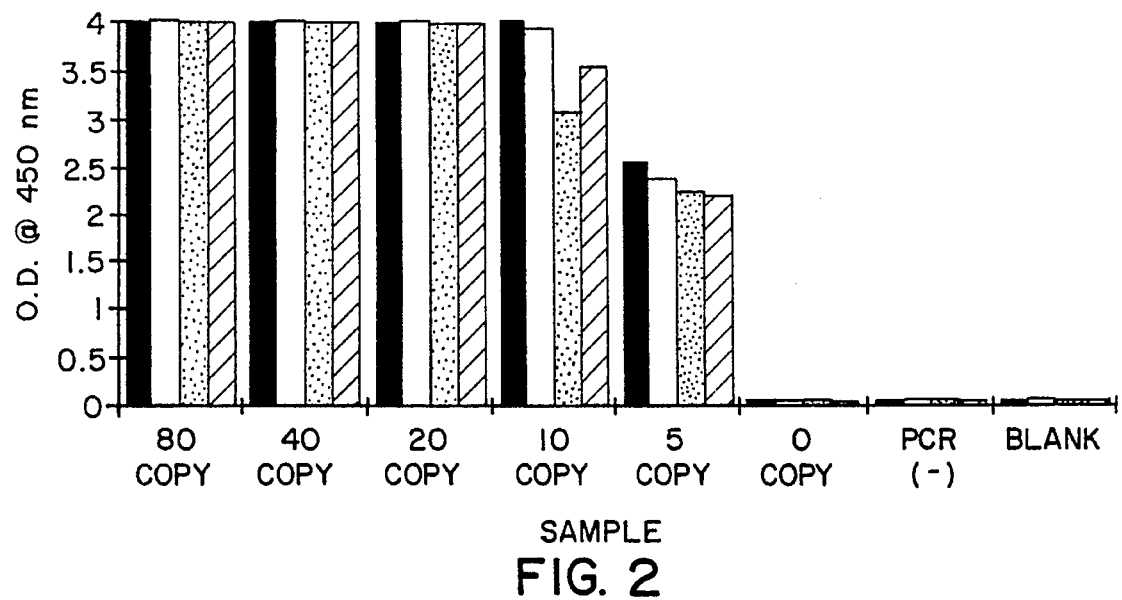
FIG. 2 shows the results of a dilution series assay to determine the sensitivity of probe PC102 (SEQ ID No. 8).

The analytical sensitivity of the amplification and detection assay was determined using samples containing low copy numbers of the plasmid, pSSP1, as described in Example 9, above. A series of samples were created from two-fold dilutions of a stock solution of pSSP1 containing from 80 copies to 5 copies per 50 µl in a background of 2 ng/µl human placental DNA. The samples were amplified in quadruplicate with primers PC41 (SEQ ID No. 4)/PC22 (SEQ ID No. 5) as described in Example 2, above. Amplification products were analyzed both by gel electrophoresis and by the microwell plate hybridization assay (probe PC102 [SEQ ID No. 8]) as described in Example 5, above. For the electrophoretic analysis, 5 µl of the PCR product were nm on an ethidium bromide-stained agarose gel. Microwell plate detection was performed with 12.5 µl of the PCR product. Amplified product was detectable even from 5 plasmid copies by both gel electrophoresis and by the microwell plate assay. Negative controls showed no signal and plate background levels were minimal. Results (4 replicates each) are shown in FIG. 2. Since the P. carinii genome is estimated to contain 16 copies of the rRNA gene per haploid genome, the equivalent of one organism was detected.

EXAMPLE 12

Specificity

A study was performed to test the specificity of amplification and microwell detection. DNA extracts from five fungi, Blastomyces dermititidis, Candida albicans, Coccidioides immitis, Histoplasma capsulatum, and Saccharomyces cerevisiae; two protozoa, Giardia lamblia and Toxoplasma gondii; and a 1 µl human genomic DNA sample were amplified with primers PC41 (SEQ ID No. 4) and PC22 (SEQ ID No. 5) as described in Example 2, above, and the amplification product was analyzed both by gel electrophoresis and by the microwell plate assay (probe PC102 [SEQ ID No. 8]) described in Example 5, above. Four of the fungi, Blastomyces dermatitidis, Candida albicans, Coccidioides immitis, and Histoplasma capsulatum, are found in oral or pulmonary samples from immunocompromised individuals and, hence, it is important that an assay for P. carinii be able to detect P. carinii in a coinfected sample. Positive and negative controls were included as described in Example 11, above.

Figure 3:
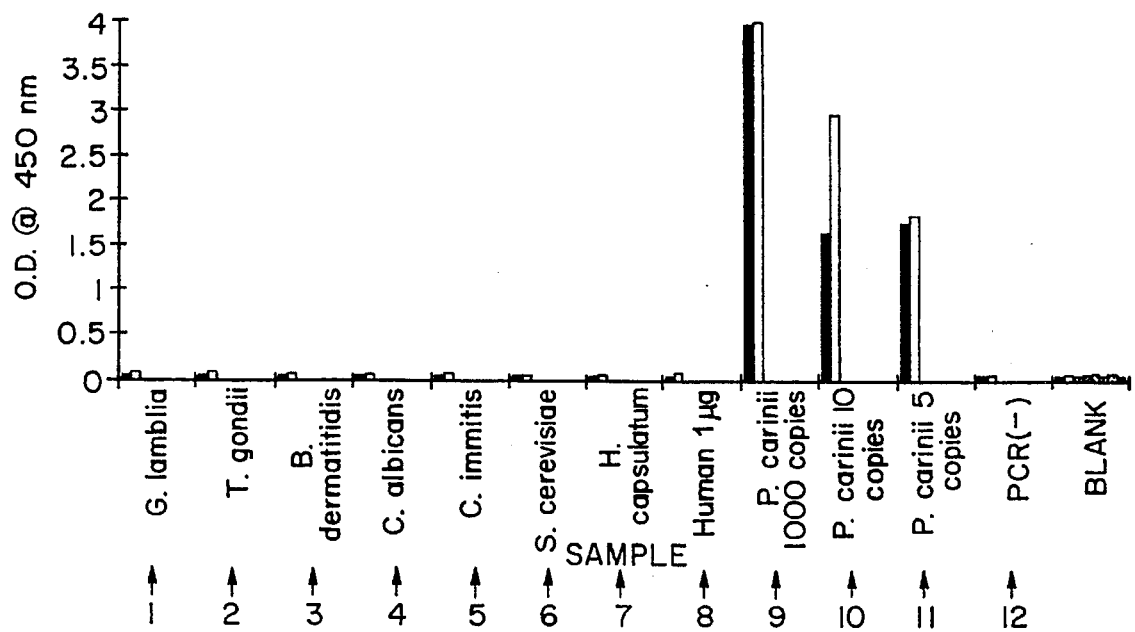
FIG. 3 shows the results of an assay of the specificity of amplification using primers PC41 (SEQ ID No. 4) and PC22 (SEQ ID No. 5).

No amplification product was detected using PC41 (SEQ ID No. 4) and PC22 (SEQ ID No; 5) from the five fungi tested, Giardia, and Toxoplasma. The sample containing 1 µg of human genomic DNA also generated no detectable amplification product. Positive controls showed expected signals, negative controls were negative, and background was minimal. Results (2 replicates each) are shown in FIG. 3.

EXAMPLE 13

Detection of Clinical Specimens

Figure 4:
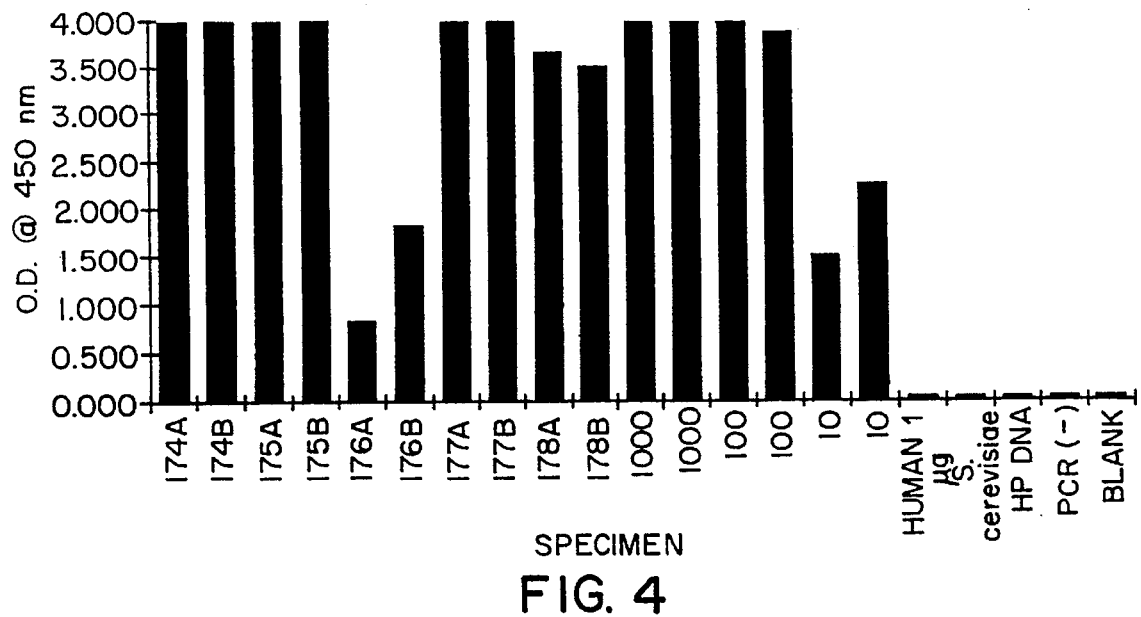
FIG. 4 shows the results of an assay for detecting *P. carinii* in clinical samples. The assay comprises amplification with the primer pair PC41 (SEQ ID No. 4)/PC22 (SEQ ID No. 5) and microwell plate detection using the probe PC102 (SEQ ID No. 8).

Five clinical specimens known to be positive for P. carinii were used in a detection assay. Amplification with primers PC41 (SEQ ID No. 4) and PC22 (SEQ ID No. 5) was as described in Example 2, above. Detection using a microwell plate passively coated with probe PC102 (SEQ ID No. 8)

was performed as described in Example 5, above. Additional samples were assayed as positive and negative controls. For positive controls, 1000, 100, and 10 copies of the pSSP1 vector; for negative controls, 1 µg human genomic DNA, 5000 copies of Saccharomyces cerevisiae DNA, 50 ng human placental DNA, and water (PCR negative). Results (2 replicates each, designated A and B ) are shown in FIG. 4. All clinical samples produced strong hybridization signals with the exception of sample 176, which showed a weaker but obviously positive signal (well over background levels). Negative controls produced no signal. Background levels were minimal.

In further experiments, 88 clinical specimens from individuals having a presumptive diagnosis of *P. carinii* pneumonia (PCP) were assayed as described above. Of these 88 samples, 48 had been found to be positive for *P. carinii* by microscopy. *P. carinii* nucleic acid was detected in all 48 samples. Of the remaining 40 samples in which no evidence of *P. carinii* was observed by microscopy, 23 were found to contain *P. carinii* nucleic acid. The methods of the present invention are significantly more sensitive than microscopy in detecting the presence of *P. carinii*. Because of the unknown rate of misdiagnosis, the observation that 17 samples were negative both by microscopy and by the methods of the current invention does not indicate a false negative result. These samples may, indeed, be negative for *P. carinii*.

EXAMPLE 14

Oligonucleotides

Other oligonucleotides which may be useful in practicing the methods of the present invention are provided below.

TABLE 5

| Primer | SEQ ID No. | Sequence |
|---|---|---|
| | | Upstream Primers |
| PC33 | 17 | 5'-TGGTTGCCTGGTCCTCCGAAGT |
| PC25 | 18 | 5'-CTCGTAGTTGAATTTAGGGATTGGTTGC |
| PC35 | 19 | 5'-CTCGTAGTTGAATTTAGGGAATGGTTGC |
| PC27 | 20 | 5'-GCTAATACATGCTAAAAATCCCGACTTTAT |
| CUTPC25 | 21 | 5'-AAAGGTACCGTCGACTCGTAGTTGAATTTAGGGATTGGTTGC |
| CUTPC27 | 22 | 5'-AAAGGTACCGTCGACGCTAATACATGCTAAAAATCCCGACTTTAT |
| FP3 | 23 | 5'-GGGGGGAGTATGGTCGCAAG |
| | | Downstream Primers |
| FP4 | 24 | 5'-GACCTBTTATTGCCTCAAACTTCC |
| FP5 | 25 | 5'-TAGCGCGCGTGCGGCCCAGA |
| PC24 | 26 | 5'-CTCATAAGATGCCGAGCGAGTCAAG |
| PC26 | 27 | 5'-GAAAGAGCTCTCAATCTGTCAATCCTTACTA |
| PC36 | 28 | 5'-GAAAGAGGTCTCAATCTGTCAATCCTTACTA |
| | | Probe |
| RDR480 | 29 | 5'-GGAAACTCACCAGGTCCAGACAAAA |

Upstream primers CUTPC25 (SEQ ID No. 21) and CUTPC27 (SEQ ID No. 22) have the same hybridizing sequences as PC25 (SEQ ID No. 18) and PC27 (SEQ ID No. 20), but include Kpn I and Sal 1 restriction sites and may be useful in cloning amplified product. Primers FP3 (SEQ ID No. 23), FP4 (SEQ ID No. 24), FP5 (SEQ ID No. 25), and the probe, RDR480 (SEQ ID No. 29), hybridize to conserved regions of the 18S rRNA gene and hybridize to most fungi.

We claim:

1. A pair of oligonucleotide primers between 15 and 40 nucleotides in length consisting of a first primer exactly complementary to SEQ ID No. 1 and a second primer exactly complementary to the complement of SEQ ID No. 1, wherein said first primer comprises a subsequence of PC22 (SEQ ID No. 5) at least 15 nucleotides in length and said second primer comprises a subsequence of PC41 (SEQ ID No. 4) at least 15 nucleotides in length.

2. A pair of oligonucleotide primers of claim 1, wherein said second primer is PC41 (SEQ ID No. 4), and wherein said first primer is PC22 (SEQ ID No. 5).

3. A plasmid vector containing a subsequence of SEQ ID No. 1, wherein said subsequence comprises bases 494 to 911 of SEQ ID No. 1.

4. A plasmid vector of claim 3, wherein said subsequence consists of SEQ ID No. 1.

5. A process for detecting nucleic acid from *Pneumocystis carinii* contained in a sample comprising:
   (a) carrying out a polymerase chain reaction using pair of oligonucleotide primers between 15 and 40 nucleotides in length consisting of a first primer exactly complementary to SEQ ID No. 1 and a second primer exactly complementary to the complement of SEQ ID No. 1, wherein said first primer comprises a subsequence of PC22 (SEQ ID No. 5) at least 15 nucleotides in length and said second primer comprises a subsequence of PC41 (SEQ ID No. 4) at least 15 nucleotides in length;
   (b) mixing said nucleic acid amplified in step (a) with an oligonucleotide probe between 10 and 50 nucleotides in length consisting of a nucleic acid sequence exactly complementary to a region of SEQ ID No. 1, wherein said region encompasses a base position of SEQ ID No. 1 selected from the group consisting of base positions 508, 540, 632, 668, 778, 837, 855, 856, 857, 858, 862, 863, 876, 878 and 884, or the exact complement thereof; and
   (c) detecting hybrids formed between said nucleic acid and said probe, which indicate the presence of said nucleic acid *Pneumocystis carinii*.

6. The process of claim 5, wherein said second primer is PC41 (SEQ ID No. 4) and said first primer is PC22 (SEQ ID No. 5).

7. The process of claim 5, wherein said oligonucleotide probe is PC 102 (SEQ ID No. 8) or the complement thereof.

8. The process of claim 5, wherein said pair of primers consists of PC41 (SEQ ID No. 4) and PC22 (SEQ ID No. 5), and wherein the probe consists of PC102 (SEQ ID No. 8), or the complement thereof.

9. A kit for detecting *Pneumocystis carinii* nucleic acid in a sample comprising an oligonucleotide probe selected from the group consisting of PC102 (SEQ ID No. 8), PC104 (SEQ ID No. 9), PC106 (SEQ ID No. 10), PC108 (SEQ ID No. 11), PC110 (SEQ ID No. 12), PC112 (SEQ ID No. 13), and sequences complementary thereto; and a pair of primers consisting of PC41 (SEQ ID No. 4) and PC22 (SEQ ID No. 5).

10. A kit of claim 9, wherein said probe consists of PC102 (SEQ ID No. 8), or the complement thereof.

11. The kit according to claim 9, further comprising a plasmid vector containing a subsequence of SEQ ID No. 1, wherein said subsequence comprises bases 494 to 911 of SEQ ID No. 1.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 951 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TGTTGGTTTC  TAGGACCCCT  GAATGATTAA  TAGGGACAGT  TGGGGGCATT  AGTATTCAAT   60
TGTCAGAGGT  GAAATTCTTA  GATTTATTGA  AGACTAACTA  CTGCGAAAGC  ATTTGCCAAG  120
GATGTTTTCA  TTAATCAAGA  ACGAAAGTTA  GGGGATCGAA  GACGATCAGA  TACCGTCGTA  180
GTCTTAACCA  TAAACTATGC  CGACTAGAGA  TCGGGCGATG  TTTTTTTCTT  GACTCGCTCG  240
GCATCTTATG  AGAAATCAAA  GTCTTCGGGT  TCCGGGGGGA  GTATGGTCGC  AAGGCTGAAA  300
CTTAAAGGAA  TTGACGGAAG  GGCACCACCA  GGAGTGGAGC  CTGCGGCTTA  ATTTGACTCA  360
ACACGGGGAA  ACTCACCAGG  TCCAGACATA  GTAAGGATTG  ACAGATTGAG  AGCTCTTTCT  420
TGATTCTATG  GGTGGTGGTG  CATGGCCGTT  CTTAGTTGGT  GAAGTGATTT  GTCTGCTTAA  480
TTGCGATAAC  GAACGAGACC  TTAACCTACT  AAATAGCCAG  ATTAGCTTTT  GCTGATCGCA  540
GGCTTCTTAG  AGGGACTGTT  GGCATGAAGC  CAATGGAAGT  TTGAGGCAAT  AACAGGTCTG  600
TGATGCCCTT  AGATGTTCTG  GGCCGCACGC  GCGCTACACT  GACAGAGCCA  GCAAGTTCAT  660
TTCCTTGACC  GAAAGGTTTG  GGTAATCTTG  TGAAACTCTG  TCGTGCTGGG  GATAGAGCAT  720
TGCAATTATT  GCTCTTCACC  GAGGAATTCC  TAGTAAGCGC  AAGTCATCAG  CTTGCGTTGA  780
TTATGTCCCT  GCCCTTTGTA  CACACCGCCC  GTCGCTACTA  CCGATTGAAT  GGCTTAGTGA  840
GGTCTTCGGA  CTGGCAGCGG  GCTGTTGGCA  ACGATGACCC  ATTGCTGGAA  AGTTGATCAA  900
ATTTGGTCAT  TTAGAGGAAG  TAAAAGTCGC  HACAAGGTTT  CCGNAGGTGA  A            951
```

( 2 ) INFORMATION FOR SEQ ID NO: 2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 2:

```
CGAGACCTTA  ACCTGCTAAA  TAGCCAGATT  A                                    31
```

( 2 ) INFORMATION FOR SEQ ID NO: 3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 3:

CGAGACCTTA ACCTGCTAAA TAGCCAGATT                              30

( 2 ) INFORMATION FOR SEQ ID NO: 4:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 4:

CGAGACCTTA ACCTACTAAA TAGCCAGATT A                            31

( 2 ) INFORMATION FOR SEQ ID NO: 5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 5:

AATGACCAAA TTTGATCAAC TTTCCAGCAA                              30

( 2 ) INFORMATION FOR SEQ ID NO: 6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 6:

AATGACCAAA TTTGAACAAC TTTCCAGCAA                              30

( 2 ) INFORMATION FOR SEQ ID NO: 7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 7:

AATGACCAAA CTTGAACAAC TTTCCAGCAA                              30

( 2 ) INFORMATION FOR SEQ ID NO: 8:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 8:

TCATCGTTGC CAACAGCCCG CTGCCAGT                                28

( 2 ) INFORMATION FOR SEQ ID NO: 9:

( i ) SEQUENCE CHARACTERISTICS:
   ( A ) LENGTH: 22 base pairs
   ( B ) TYPE: nucleic acid
   ( C ) STRANDEDNESS: single
   ( D ) TOPOLOGY: linear ( i i ) MOLECULE TYPE: genomic DNA ( x i ) SEQUENCE DESCRIPTION: SEQ ID NO: 9:

TTGCCAACAG CCCGCTGCCA GT    22

( 2 ) INFORMATION FOR SEQ ID NO: 10:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 10:

GCTGCCAGTC CGAAGACCTC ACTAA    25

( 2 ) INFORMATION FOR SEQ ID NO: 11:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 11:

CGAAGACCTC ACTAAGCCAT TCAAT    25

( 2 ) INFORMATION FOR SEQ ID NO: 12:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 12:

TCAAGGAAAT GAACTTGCTG GCTCT    25

( 2 ) INFORMATION FOR SEQ ID NO: 13:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: genomic DNA ( x i ) SEQUENCE DESCRIPTION: SEQ ID NO: 13:

TTCGGTCAAG GAAATGAACT TGCTGGCTCT    30

( 2 ) INFORMATION FOR SEQ ID NO: 14:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear (ii) MOLECULE TYPE: genomic DNA (xi) SEQUENCE DESCRIPTION: SEQ ID NO: 14:

TCCGCAGGTT CACCTACGGA                                              20

(2) INFORMATION FOR SEQ ID NO: 15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 15:

GTGGTTCTAT TTTGTTGGTT TCTA                                         24

(2) INFORMATION FOR SEQ ID NO: 16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 16:

TGGTTGCCTG GTCCTCCGAA G                                            21

(2) INFORMATION FOR SEQ ID NO: 17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 17:

TGGTTGCCTG GTCCTCCGAA GT                                           22

(2) INFORMATION FOR SEQ ID NO: 18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 18:

CTCGTAGTTG AATTTAGGGA TTGGTTGC                                     28

(2) INFORMATION FOR SEQ ID NO: 19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 19:

CTCGTAGTTG AATTTAGGGA ATGGTTGC                                                                                  28

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 20:

GCTAATACAT GCTAAAAATC CCGACTTTAT                                                                                30

(2) INFORMATION FOR SEQ ID NO: 21:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 21:

AAAGGTACCG TCGACTCGTA GTTGAATTTA GGGATTGGTT GC                                                                  42

(2) INFORMATION FOR SEQ ID NO: 22:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 22:

AAAGGTACCG TCGACGCTAA TACATGCTAA AAATCCCGAC TTTAT                                                               45

(2) INFORMATION FOR SEQ ID NO: 23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 23:

GGGGGGAGTA TGGTCGCAAG                                                                                           20

(2) INFORMATION FOR SEQ ID NO: 24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 24:

GACCTBTTATTGCCTCAAACTTCC                                                                                        24

(2) INFORMATION FOR SEQ ID NO: 25:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 25:

TAGCGCGCGT GCGGCCCAGA 20

( 2 ) INFORMATION FOR SEQ ID NO: 26:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 26:

CTCATAAGAT GCCGAGCGAG TCAAG 25

( 2 ) INFORMATION FOR SEQ ID NO: 27:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 27:

GAAAGAGCTC TCAATCTGTC AATCCTTACT A 31

( 2 ) INFORMATION FOR SEQ ID NO: 28:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 28:

GAAAGAGGTC TCAATCTGTC AATCCTTACT A 31

( 2 ) INFORMATION FOR SEQ ID NO: 29:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: genomic DNA ( x i ) SEQUENCE DESCRIPTION: SEQ ID NO: 29:

GGAAACTCAC CAGGTCCAGA CAAAA 25